United States Patent [19]

Harris et al.

[11] Patent Number: 4,570,625
[45] Date of Patent: Feb. 18, 1986

[54] APPARATUS FOR EXTERNAL FIXATION OF BONE FRACTURES

[75] Inventors: John D. Harris, Abingdon; Mervyn Evans, Kidlington, both of England

[73] Assignee: National Research Development Corporation, London, England

[21] Appl. No.: 662,551

[22] Filed: Oct. 19, 1984

Related U.S. Application Data

[62] Division of Ser. No. 404,498, Aug. 2, 1982, Pat. No. 4,502,473.

[30] Foreign Application Priority Data

Aug. 6, 1981 [GB] United Kingdom ............... 8124043

[51] Int. Cl.⁴ .............................................. A61F 5/04
[52] U.S. Cl. ................................. 128/92 G; 128/92 A
[58] Field of Search ............... 128/92 R, 92 A, 92 G, 128/92 C, 84 R, 84 C

[56] References Cited

U.S. PATENT DOCUMENTS

| 2,204,266 | 6/1946 | Wilcox | 128/92 A |
| 2,333,033 | 10/1943 | Mraz | 128/92 A |
| 2,391,537 | 12/1945 | Anderson | 128/92 A |
| 3,977,397 | 8/1976 | Kalnberg et al. | 128/92 A |
| 4,024,860 | 5/1977 | Chenokov et al. | 128/92 A |
| 4,187,841 | 2/1980 | Knutson | 128/92 E |
| 4,220,146 | 9/1980 | Cloutier | 128/69 |
| 4,271,823 | 6/1981 | Evans et al. | 128/92 A |
| 4,502,473 | 5/1985 | Harris | 128/92 A |

FOREIGN PATENT DOCUMENTS

| 1569090 | 5/1969 | France . |
| 1492681 | 1/1975 | United Kingdom . |
| 1472097 | 4/1977 | United Kingdom . |

Primary Examiner—Robert Peshock
Assistant Examiner—C. W. Shedd
Attorney, Agent, or Firm—Cushman, Darby & Cushman

[57] ABSTRACT

A non-rigid bone fracture fixator comprising first and second bone pins for connection either side of a bone fracture and primary and secondary supports clamped to the bone pins by respective fixed and guide clamps. The second support and the guide clamps are connected slidably to the primary support such that the supports may execute a controlled degree of movement with respect to one another. A compression spring is arranged to bias apart the supports longitudinally of a fixated limb. In use the fixator is applied to the limb with the fracture in slight compression. Exercise of the limb then produces varying degrees of fracture compression stimulating bone callus formation and rapid healing. The fixator may include actuating means to provide passive fracture exercise for immobilized patients.

5 Claims, 15 Drawing Figures

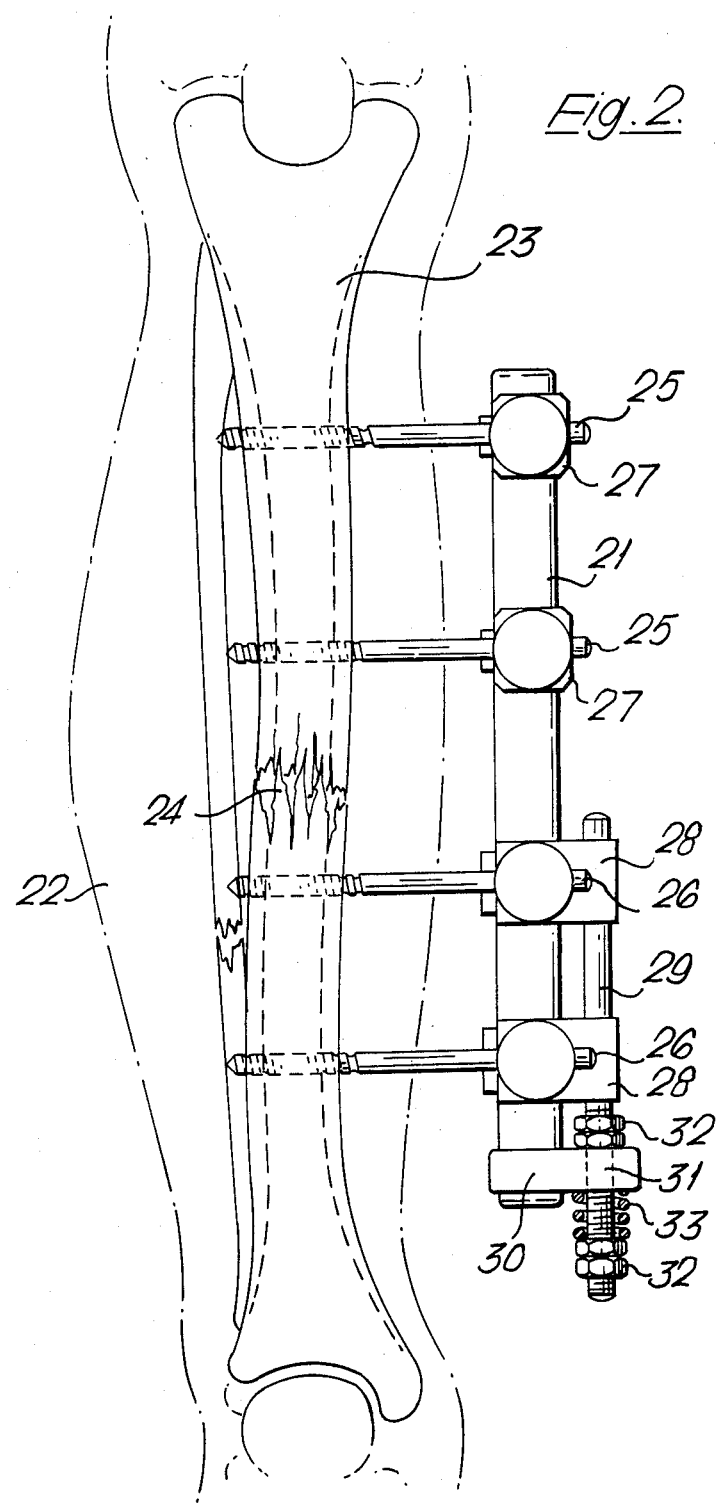

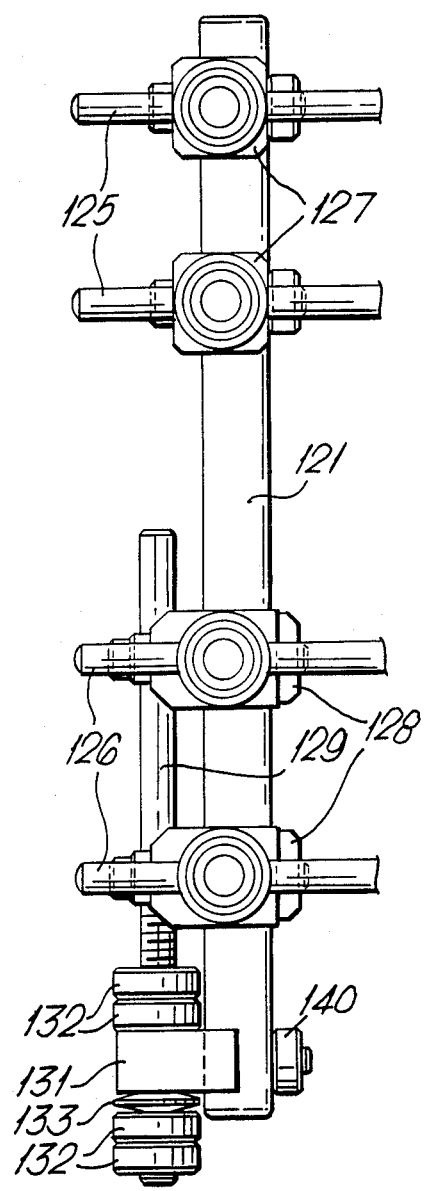
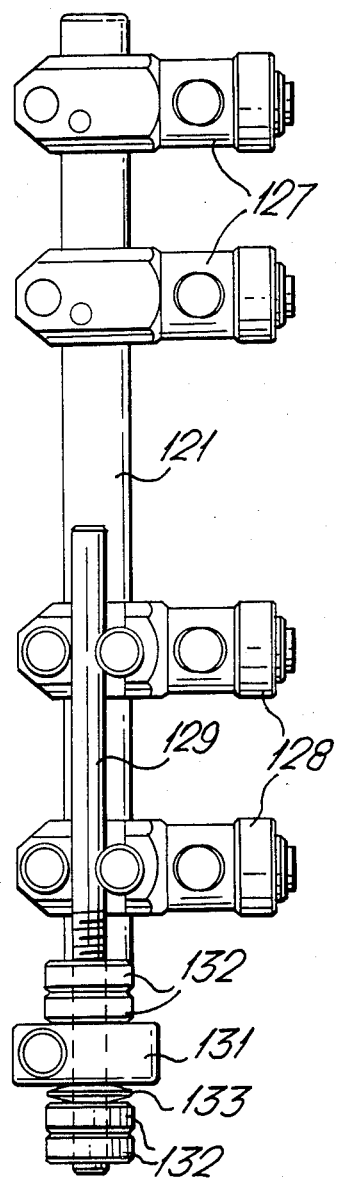

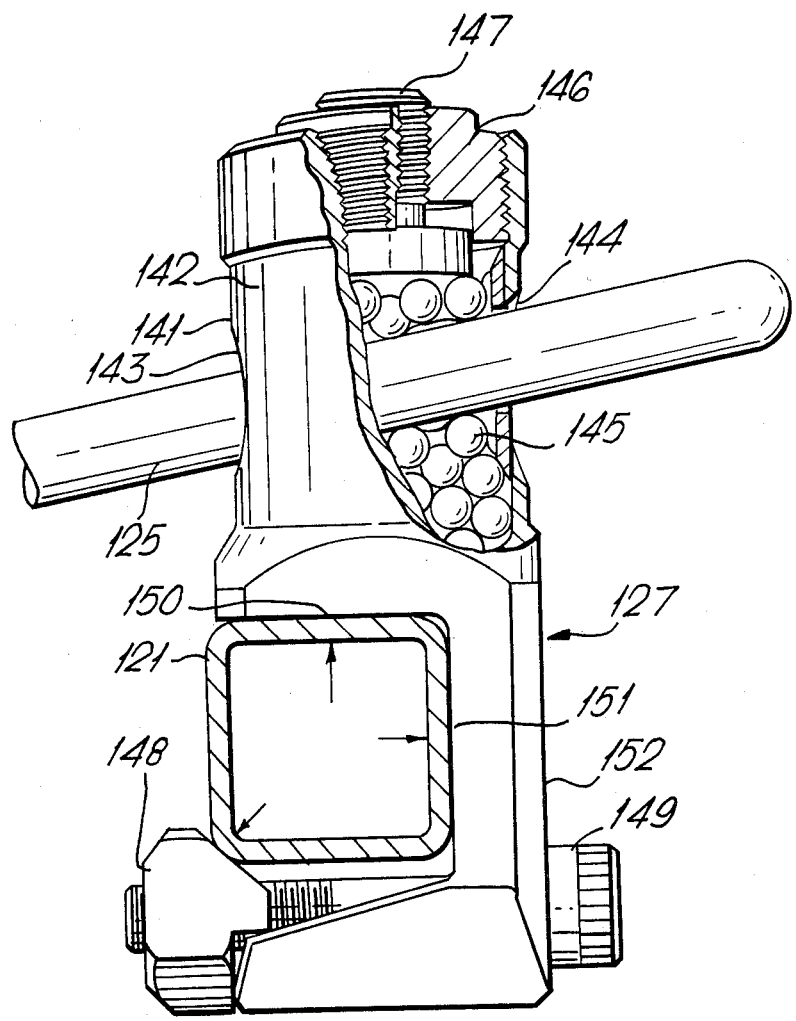

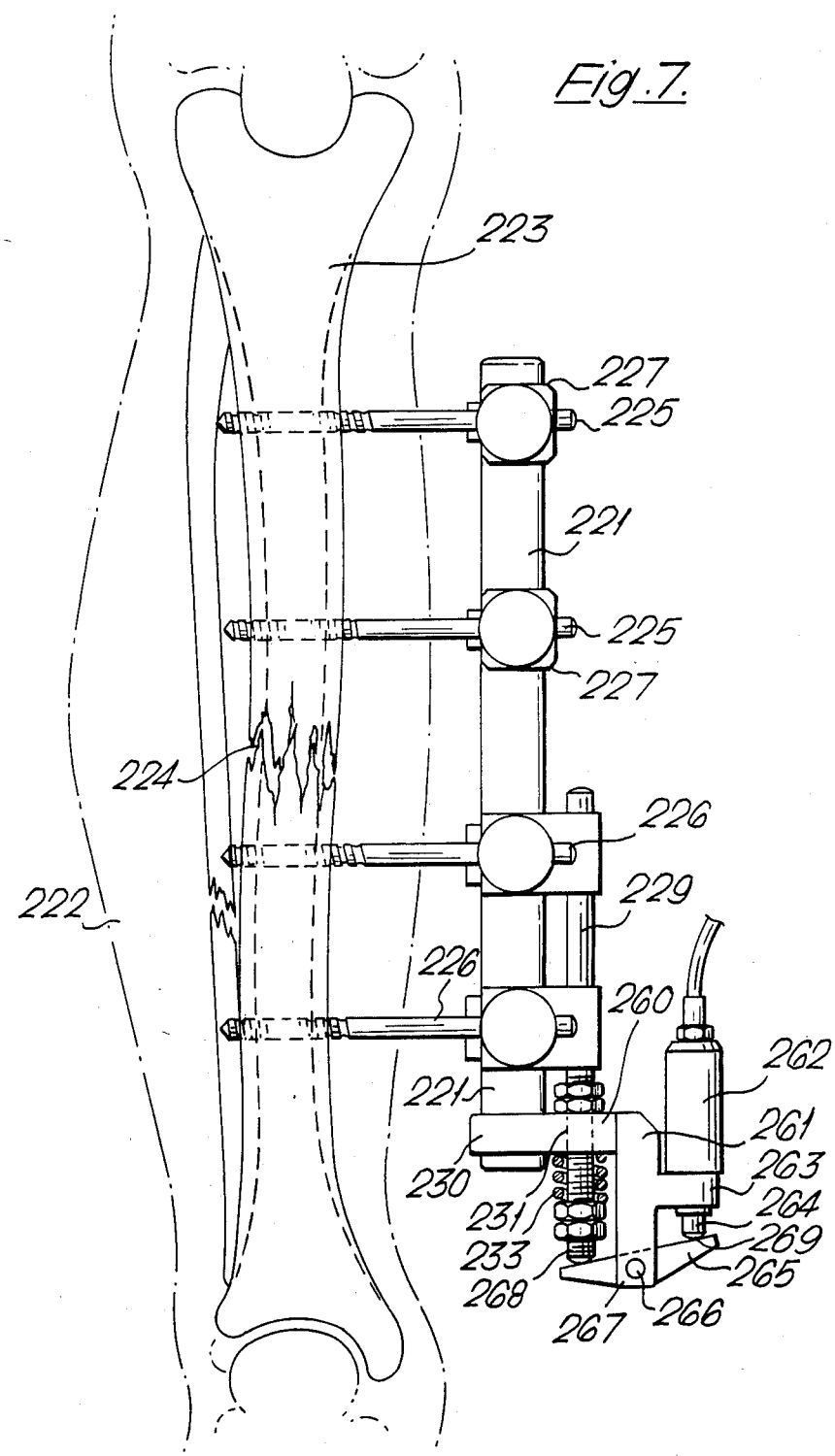

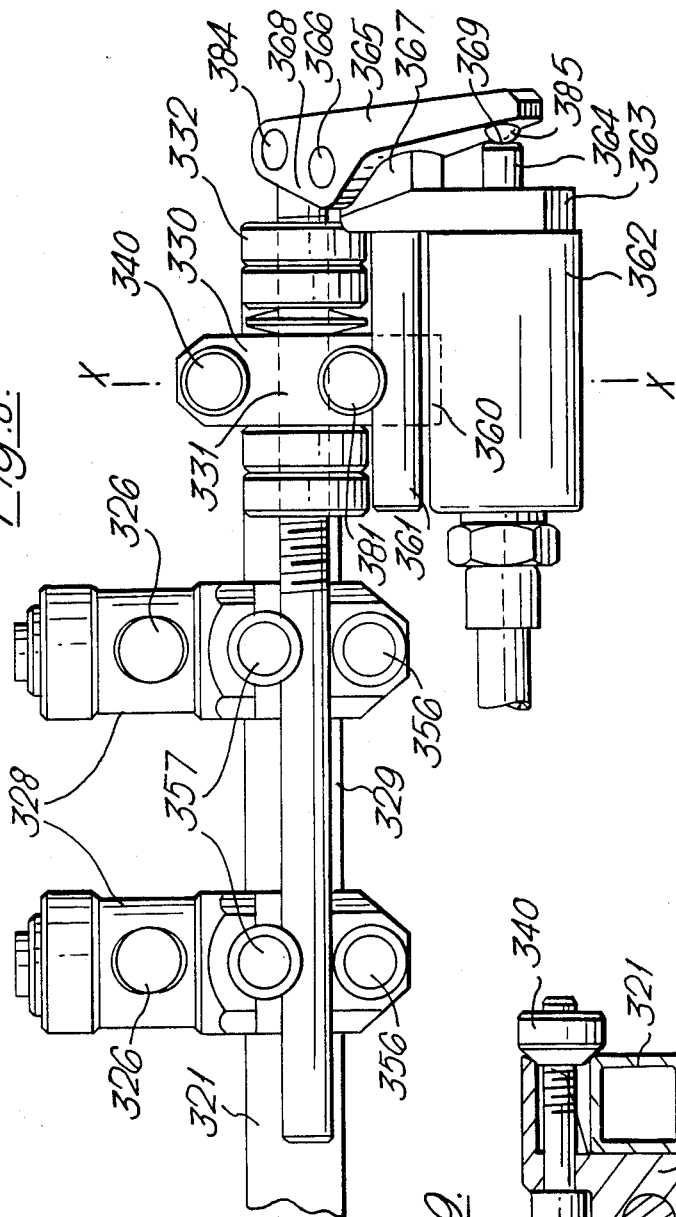
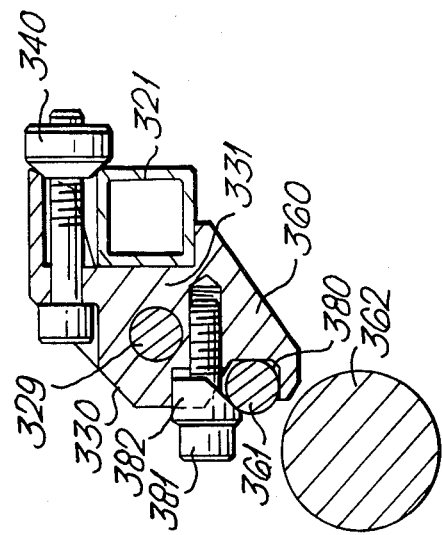

APPARATUS FOR EXTERNAL FIXATION OF BONE FRACTURES

This is a division of application Ser. No. 404,498, filed Aug. 2, 1982, now U.S. Pat. No. 4,502,473.

This invention relates to apparatus for external fixation of bone fractures during bone healing.

As is well-known in medical science, in order to obtain acceptable bone union it is necessary to preserve the appropriate bone geometry at the fracture site. For this purpose it is known to employ plaster casts for simple or comparatively minor fractures. For more complex or serious fractures, rigid or flexible clamping devices such as bone plates or external fixators have been employed. Conventional bone plates are screwed to the bone fracture parts across the fracture site. External fixators consist of one or more supports located externally of the broken limb clamped to bone pins extending through the skin to each of the bone parts of the fracture. The bone pins connect and locate in position the broken bone portions at the fracture site, as described for example in applicant's co-pending UK Application No. 7924853.

It is well-known that primary bone healing may be preceded by the formation of bone callus over the fracture site. Callus forms much more rapidly than new primary bone, and affords a natural stabilising layer over the fracture under which new bone may form. However, whereas callus formation is often experienced with fractures which are retained in plaster casts, it is found that the use of bone plates or rigid external fixators does not encourage callus formation. Accordingly, use of bone plate or rigid external fixator may require many months to heal a bone fracture by new primary bone formation. This is highly disadvantageous since both bone plates and fixator bone pins are surgically inserted under or through the skin of the broken limb with consequent infection risk. Accordingly, the greater the time required for healing the greater the risk of infection due to the bone plate or pin. However, there are many bone fracture cases in which a plaster cast is inadequate, and hitherto the the time deficiencies of bone plates or external fixators have been tolerated.

It is also know to employ flexible external fixators to aid fracture healing. However, it has been found that prior art flexible fixators may give inadequate mechanical stability to a fractured limb, with consequent risk of refracture or misalignment of a healing fracture.

It is an object of the present invention to provide an improved form of external fixator adapted to encourage bone callus formation.

The present invention provides an external fixator comprising a plurality of first bone pins for connection to a first bone portion, primary rigid external bone pin support means for connection to the first bone pins, a plurality of second bone pins for connection to a second bone portion, secondary rigid external bone pin support means for connection to the second bone pins, and connecting means for connecting the primary and secondary support means, the connecting means being adapted, when subjected in use to a normal fracture exercise load cycle, to allow relative movement between the first and second bone pins to a degree sufficient to encourage callus formation between the bone portions but insufficient to effect permanent fracture misalignment or to inhibit primary bone formation.

It has been found that controlled relative movement between the first and second bone pins, which promotes callus formation, can be achieved with a fixator of the invention whilst retaining sufficient rigidity to preserve bone alignment and primary bone growth, unlike prior art flexible fixators. Moreover, the necessary relative movement may be produced merely by exercising the fracture, for example by active stimulation ie a patient walking on a factured leg. This is highly advantageous, since the time required to achieve a load-bearing healed fracture is reduced as compared to that needed for primary bone growth by prior art rigid fixator or bone plate techniques.

In practice, the invention may be used for example to set a fractured limb. A surgeon would insert the first and second bone pins in the first and second bone portions either side of a fracture site. He would then connect the primary and secondary bone support means with the connecting means and adjust them until the fracture site experiences slight compression when not under exercise loading. A fracture exercise load cycle would normally involve varying degrees of fracture compression only, it being considered desirable to avoid fracture site extension.

The said degree of relative movement between the bone pins may be up to 2.00 mm when measured between first and second bone pins at their connections to the primary and secondary support means respectively. The corresponding movement at the fracture site may be in the range of micro-movement (small but non-zero) up to 0.5 mm approximately. Bone-pin flexure takes up a proportion of the movement. For tibial fractures, relative bone portion movement at the fracture site may be up to 0.2 mm and corresponding movement of connections at the supports may be 0.2 mm to 0.5 mm.

The connecting means preferably includes resilient biasing means arranged, when in use with the bone fracture under compressive load, to bias apart the first and second bone pins longitudinally of a fixated bone, the resilience of the biasing means being appropriate for execution of the said degree of relative movement during the load cycle longitudinally of a fixation bone.

In one embodiment of the invention, the first and second bone pins are rigidly securable to their respective primary and secondary support means by primary and secondary clamps adapted for adjustable bone pin direction; the secondary clamps are additionally mountable slidably on the primary support means, and the secondary support means are connected slidably to the primary support means, the arrangement being such that the secondary support means and secondary clamps are in use moveable and resiliently biased relative to the primary support means longitudinally of a fixation limb.

Conveniently the primary and secondary support means are elongate members for disposition substantially longitudinally of a fixation limb.

In a particularly preferred embodiment, the invention includes actuating means adapted to produce repetitively the said degree of relative movement between the first and second bone pins thereby simulating bone fracture exercise. It is considered that this aspect of the invention is particularly valuable, since it allows an immobile patient to have bone fracture exercise or passive stimulation. This produces rapid callus formation or healing in cases where patient mobility is undesirable or impossible, such as serious injury cases. Accordingly, the use of actuating means in accordance with the invention enhances healing in precisely those cases for which rapid healing is most desirable, but in which bone callus is unlikely to form by conventional healing techniques.

The actuating means is conveniently adapted both to act on the primary or secondary support means and to produce repetitive oscillatory movement therebetween longitudinally of a fixated member. The actuating means is preferably adapted to co-operate with the resilient biasing means to produce oscillatory forward and return strokes. Conveniently, the actuating means may include a pneumatic or hydraulic piston-and-cylinder arrangement adapted to introduce relative movement between the primary and secondary support means.

FIG. 2 is a schematic front elevation of an external fixator of the invention,

Figure 6:
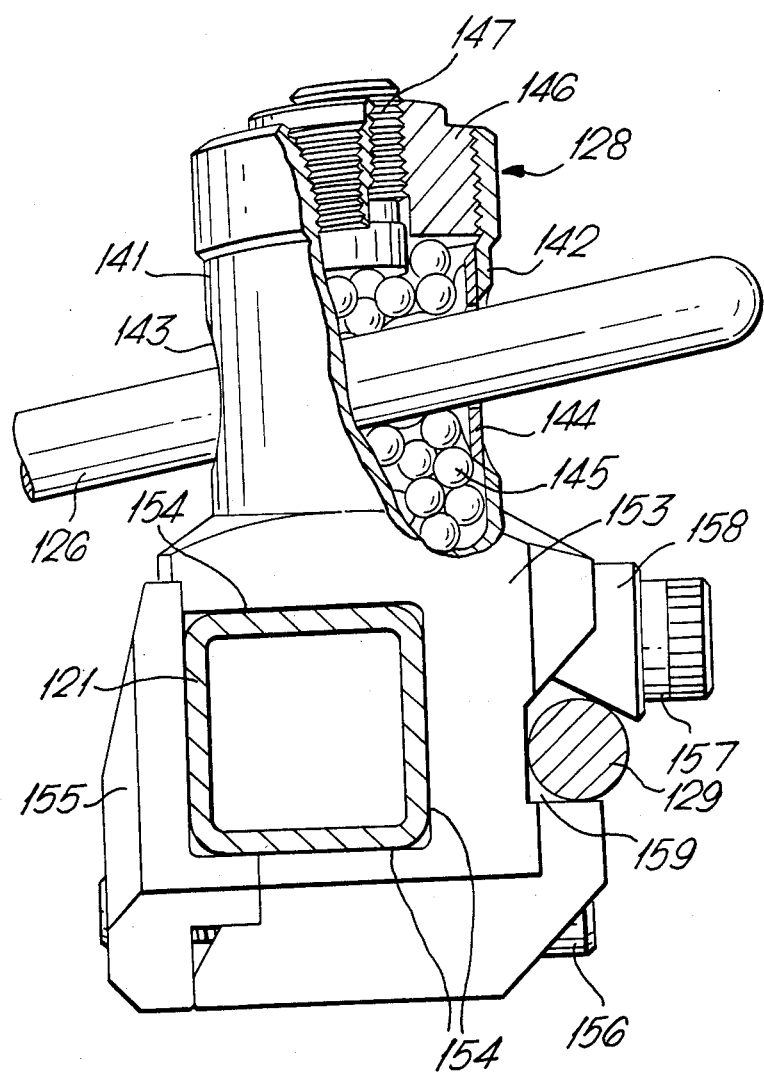
Figure 10:
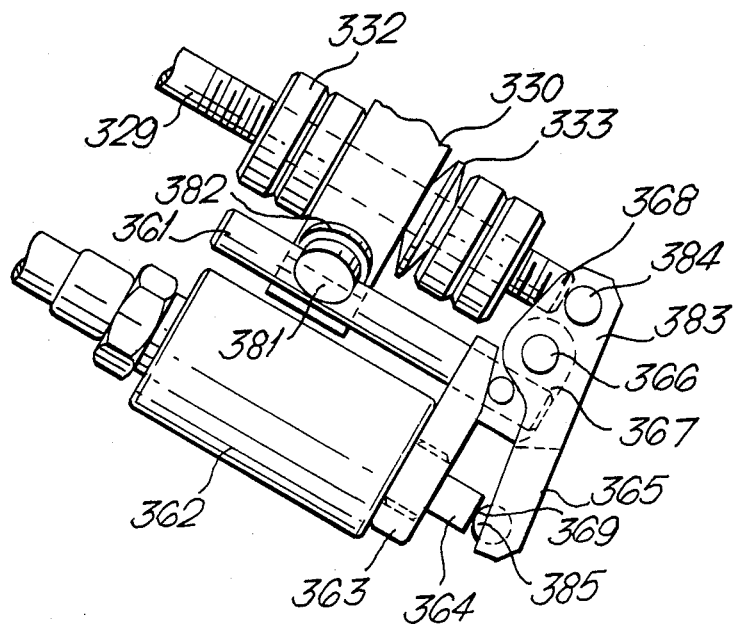
Figure 11:
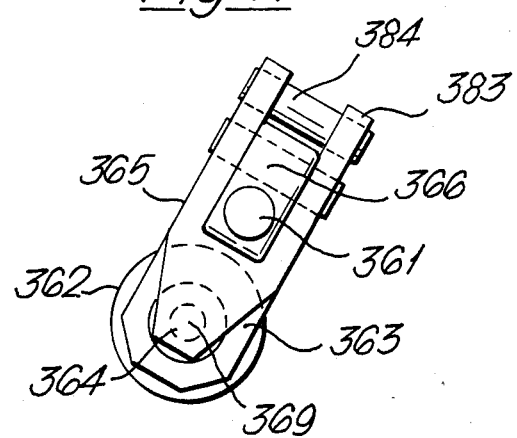
Figure 12:
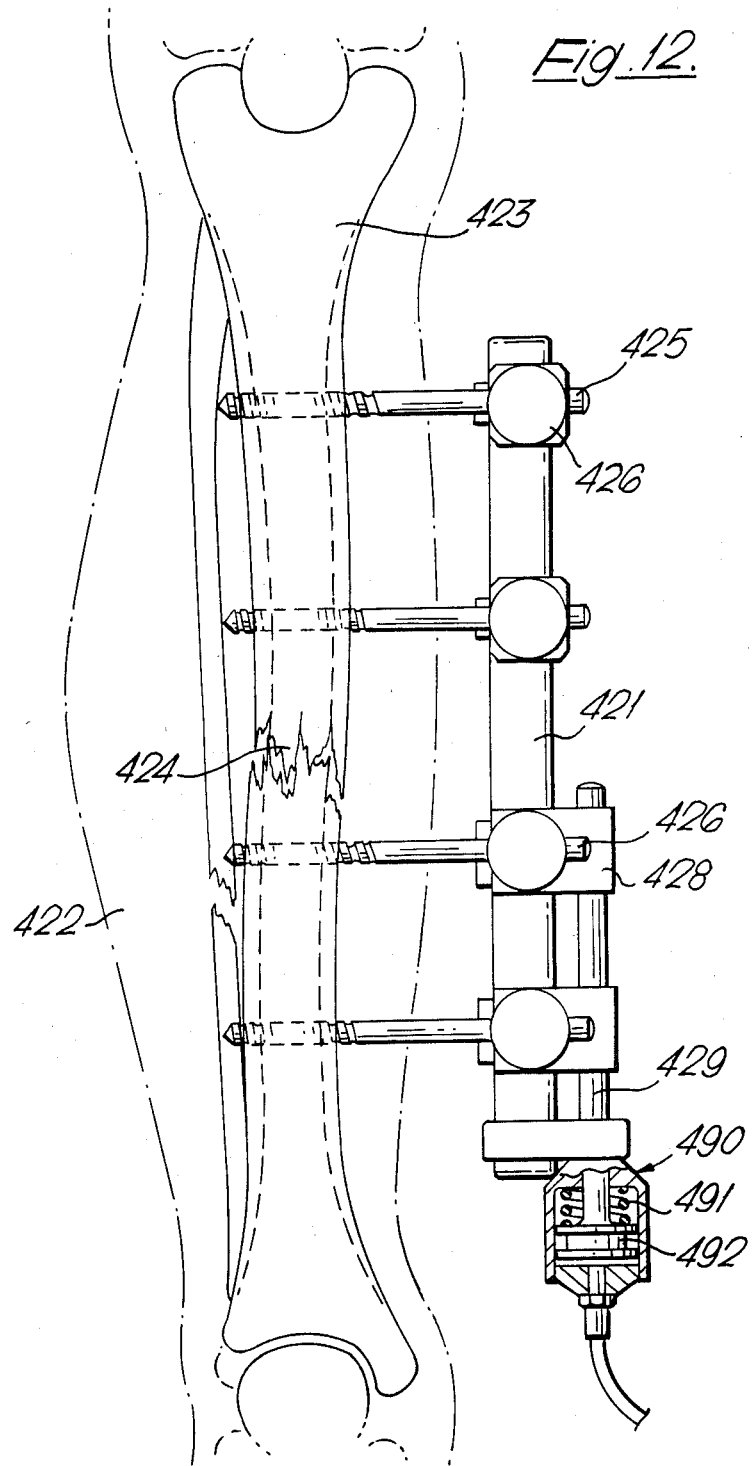
Figure 13:
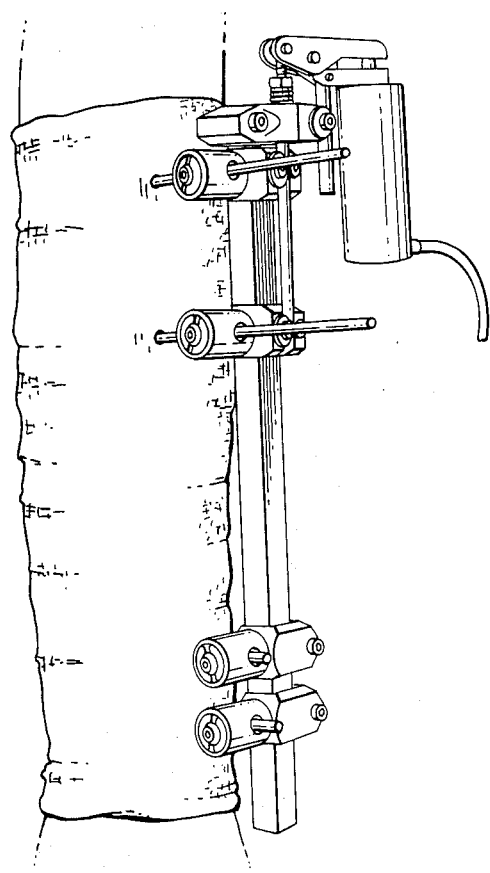
Figure 14:
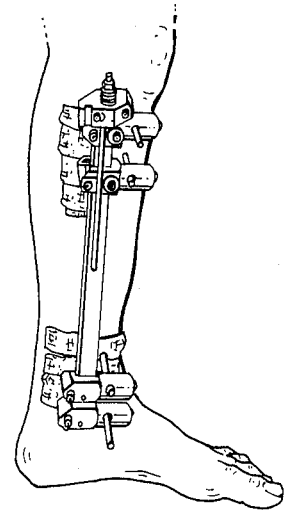
Figure 15:
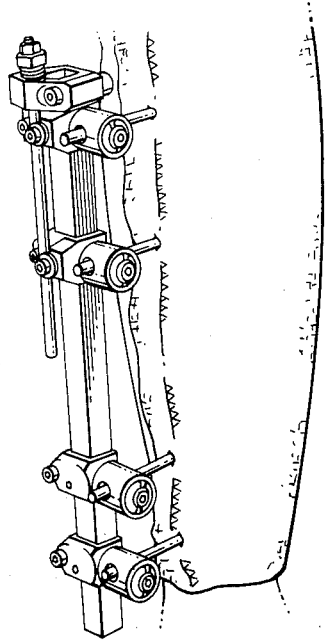

FIGS. 3 and 4 are respectively detailed front and side elevations of a fixator of the invention, FIGS. 5 and 6 are part-sectional views of fixed and guide bone pin clamps respectively, FIG. 7 is a schematic front elevation of a mechanically actuated fixator of the invention, FIG. 8 is a detailed side elevation of one end of a mechanically actuated fixator of the invention, FIG. 9 is a sectional view along lines X—X of FIG. 8, FIG. 10 is an oblique elevation of the fixator of FIG. 8, FIG. 11 is an end view of the fixator of FIGS. 8 to 10, FIG. 12 shows an alternative mechanically actuated fixator, and FIGS. 13 to 15 show fixators applied to patients.

Figure 1:
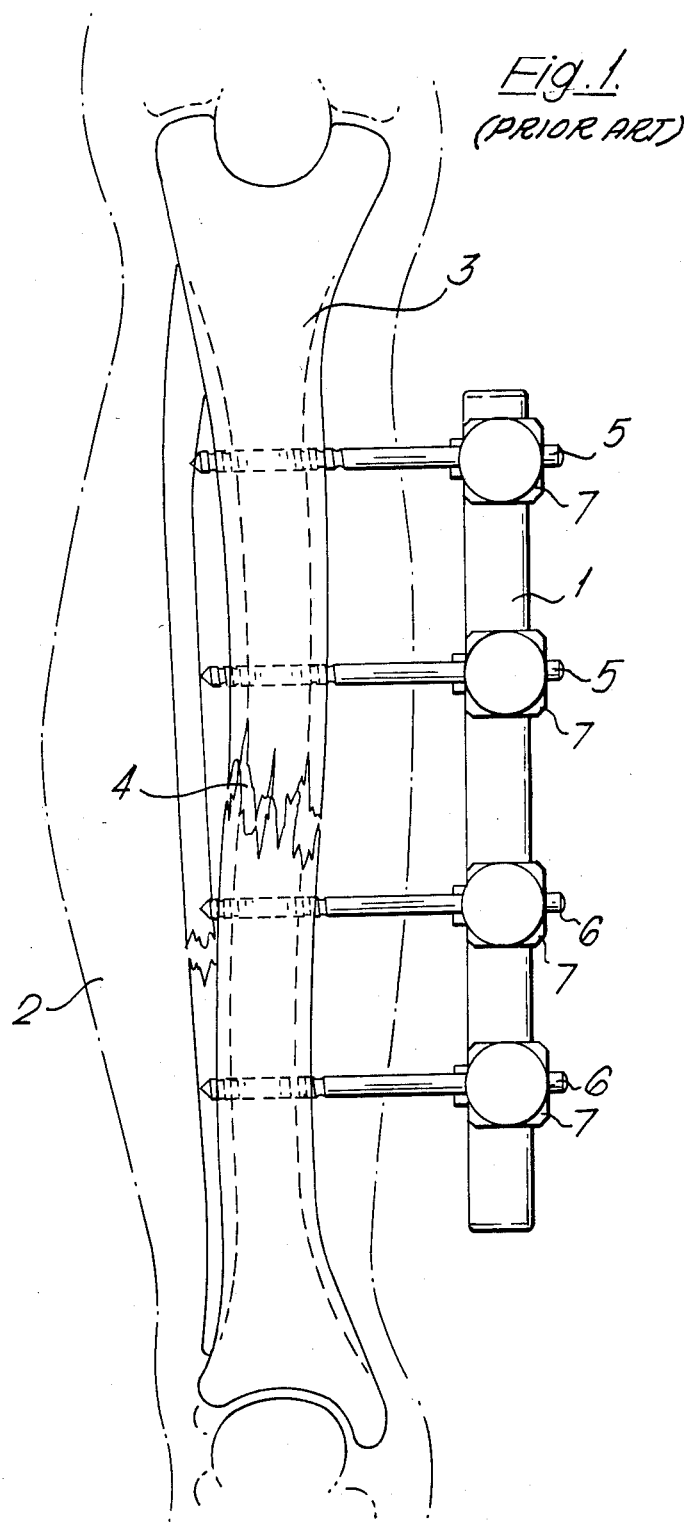
FIG. 1 is a schematic front elevation of a prior art rigid external fixator.

Referring to FIG. 1, a prior art external fixator is schematically shown of the kind described in Applicant's co-pending UK Application No. 7924853. The fixator consists of a square-section support tube 1 arranged longitudinally and externally of a human shin 2. The shin 2 has a tibia 3 with a fracture 4. Two upper bone pins 5 and two lower bone pins 6 are inserted into the tibia 3 on either side of the fracture 4. The pins 5 and 6 are rigidly secured to the support 1 by clamps 7 such that the alignment of the tibia 3 is rigidly preserved across the fracture 4 during healing.

Referring now also to FIG. 2, an external fixator of the invention is shown, parts equivalent to those shown in FIG. 1 being like-referenced with the prefix 20. Upper (or first) bone pins 25 are clamped rigidly to a primary support tube 21 by fixed clamps 27, but lower (or second) bone pins 26 are clamped to guide clamps 28 connected rigidly to a secondary support rod 29 and mounted slidably on the primary support tube 21. A slide clamp 30 is rigidly connected to the primary support 21 and includes a collar portion 31 slidably mounted on the secondary support 29. The secondary support rod 29 carries lock-nuts 32 retaining therebetween the collar 31 and a compression spring 33 located against and immediately below the collar 31. The bone pins 25 and 26 are inserted in the tibia 23 during a surgical operation, and the associated support equipment 25 and 33 are assembled such that the fracture 24 is under slight compression.

The apparatus of FIG. 2 operates as follows. The fixator apparatus is assembled on a human shin 22 by a surgeon for healing a tibial fracture 24. The assembly is such that the fracture 24 is under slight compression when unloaded. The fixator is sufficiently rigid to allow the patient to walk without adverse effects on healing. However, during walking, the fracture 24 is further compressed when bearing a patient's weight, and the upper and lower bone pins 25,26 with their attached clamps 27 and 28 are urged together. The guide clamps 28 accordingly slide upwardly on the primary support tube 21, the secondary support bar 29 moves with the guide clamps 28 upwardly with respect to the slide clamp 30 and collar 31, and the spring 33 is compressed between the collar 31 and lock-nuts 32. When weight is removed from the fracture 24, the spring 33 urges the upper and lower bone pins 25 and 26 apart longitudinally of the primary support 21. The fixator apparatus is rigid in the plane transverse to the primary support 21, but in the longitudinal direction a predetermined degree of movement of the bone fracture ends towards and away from each other is obtained for a spring 33 of given force constant and a given fracture loading by the patient's weight. It has been found that a relative movement 0.5 to 2.0 mm may be suitable between the upper and lower bone pins 25 and 26 (measured at the clamps 27 and 28). This corresponds to micro-movement (small but non-zero) up to 0.5 mm approximately at the bone fracture 24. Bone pin and associated flexure takes up residual movement. It will be appreciated that fracture movement is difficult to measure reliably through intervening flesh and skin. For a tibial fracture, up to 0.2 mm movement at the fracture and 0.2 to 0.5 mm between the clamps has been found appropriate.

Referring now also to FIGS. 3 to 6, FIG. 3 and 4 respectively show detailed front and side elevations of apparatus equivalent to that illustrated schematically in FIG. 2 and FIGS. 5 and 6 show fixed and guide clamps respectively. (NB: FIG. 3 corresponds to FIG. 2 laterally inverted.) In FIGS. 3 to 6 parts equivalent to those shown in FIG. 2 are like-referenced with the prefix 100. The primary support 191 is a square tube retaining fixed clamps 172, and the secondary support 129 is a solid rod rigidly retaining the guide clamps 128 which are slidable on the support 129. The compression spring 133 is provided by a pair of belleville spring washers arranged base to base. The use of belleville washers is advantageous since it allows the force constant of the spring 133 to be altered by changing the number and/or relative orientation of the washers. The spring 133 is retained by lock-nuts 132 against the lower side of the collar 131 of the slide clamp 130, itself secured to the primary support 121 by a nut 140.

The fixed and guide bone-pin clamps 127 and 128 have similar upper pin-clamping portions 141. The upper portions 141 each consist of a hollow barrel 142 with holes 143 and 144 centered on a diameter, and through which a sleeved pin 125 or 126 passes transversely. The barrel 142 contains ball-bearings 145 retained by a threaded cup 146 and urged into clamping contact with the sleeved pin by a locking screw 147. With the cap 146 and screw 147 partially unscrewed, the pin 125 or 126 may be set in any desired direction (within the limits set by holes 143 and 144) to pin a bone, and the pin is then clamped in that direction by screwing up the cap and screw.

The fixed clamp 127 rigidly retains the primary support tube 121 by means of a clamp plate 148 and clamp screw 149. The plate 148 and screw 149 urge the tube 121 into clamping contact with two faces 150 and 151 of the lower body portion 152 of the fixed clamp 127.

The guide clamp 128 has a lower body portion 153 having three flat surfaces 154 between which the primary support tube 121 is a sliding fit. A keep plate 155 and screw 156 retain the support 121 between the surfaces 154. The guide clamp 128 is rigidly connected to the secondary support rod 129 by means of a clamping screw 157 and locking bush 158. The screw 157 and bush 158 clamp the rod 129 into a recess 159 in the guide clamp lower body portion 153.

Referring now to FIG. 7, there is schematically shown a modification of the embodiment illustrated in FIG. 2 corresponding parts being like-referenced with the prefix 200. The slide clamp 230 is equivalent to slide clamp 30 of FIG. 2, having a central collar portion 231 slidably mounted on the secondary support rod 229 and being clamped to the primary support tube 221. The slide clamp 230 however possesses an additional clamping body portion 260 rigidly retaining a location bar 261. The location bar 261 is connected rigidly to a pneumatic cylinder 262 by means of a plate 263 through which a pneumatic piston 264 protrudes. A lever 265 is mounted pivotally at 266 on the foot 267 of the location bar 261. The lever 265 engages the lower end 268 of the secondary support rod 229. The piston 264 engages the lever 265 at 269.

The arrangement of FIG. 7 operates as follows. When the piston and cylinder arrangment (264 and 262) is pneumatically actuated, the piston 264 urges the lower 265 downwardly at 269 to pivot at 266. The lever 265 accordingly urges the secondary support rod 229 longitudinally upwards. When pneumatic pressure is reduced, the compression spring 233 actuates a return stroke of the rod 229 longitudinally downwards. This produces a compression-extension load cycle of the bone fracture 224 retained by the modified fixator. In practice, the piston is actuated repetitively at a rate appropriate to normal fracture exercise, about one cycle per second. For a tibial fracture, the piston stroke is arranged to be in the range 0.2 to 0.5 mm, so that the upper and lower bone pins 25 and 26 may move together a distance in this range measured between clamps 27 and 28.

Referring now also to FIGS. 8 to 11, there are shown detailed representations of the lower part of the fixator assembly schematically illustrated in FIG. 7 having parts detailed in FIGS. 3, 4 and 6. Parts in FIGS. 8 to 11 equivalent to those described earlier have similar references with the prefix 300 replacing 100 to 200 as appropriate. FIG. 8 is a side elevation corresponding to FIG. 4, FIG. 9 is a sectional view through the slide clamp 330 on lines X—X in FIG. 8, FIG. 10 is an oblique side elevation and FIG. 11 an end view. Parts not equivalent to those previously described are as follows. The slide clamp 330 retains the location bar 361 in a recess 380 of its body portion 360 by means of a screw 381 and locking bush 382. The lever 365 has a bifurcate end 383 retaining a lever pin 384 for engaging the lower end 368 of the secondary support rod 329. The compression spring 333 consists of a pair of belleville washers arranged bast to base. The lever 365 has a stud 385 for engaging the piston 364.

Referring now also to FIG. 12, there is shown an alternative form of mechanical actuation. Parts equivalent to those previously described have the prefix 400. The FIG. 12 arrangement is similar to that shown in FIG. 7, except that the pneumatic piston and cylinder arrangement 490 acts directly on the secondary support rod 429 instead of via a pivoted lever. The pneumatic arrangement 490 also includes an internal return spring 491 to reset the piston 492 when pneumatic pressure is reduced. Pressurising the pneumatic arrangement 490 initiates a compression-extension cycle of the fracture 424 as previously described.

Mechanical movement of a fracture employing an actuator in this fashion is advantageous in cases where it is undesirable or impossible for the patient to exercise the fracture. This is particularly important when a patient has sustained a serious injury and immobilisation is necessary. Mechanical actuation makes it possible to encourage bone callus formation, and thus rapid healing, when a conventional plaster cast might be totally inappropriate and prior art bone plate or rigid fixator techniques would require many months to achieve healing. Since any reduction in healing time reduces the risk of infection, this is regarded as an important advantage of the invention.

Whereas in FIGS. 7 to 12 a pneumatic piston and cylinder actuator has been described, it will be apparent to skilled mechanical engineers that alternative drive means may be employed. A hydraulic drive cylinder, a cam-operated or electromechanical drive may be employed for example.

The fixator of the invention has been employed in surgical operations on ten patients since November 1981. The majority of operations were for tibial fractures. However, one patient also had a fixator applied to the opposite femur, one operation was for an ununited fracture of the tibia, one replaced a splinting procedure which had given rise to soft tissue necrosis, and three were used for leg lengthening procedures, one of which involved a polio patient. This number does not allow statistical proof of improved bone union to be claimed, as all fractures were different in type and severity, and the subsequent operation and treatment significantly affect the healing of the fracture. However, the results at the very least demonstrate a degree of consolidation and healing of the fracture which, by comparison with external fixation results generally, subjectively appear to give an increased response in bone production and reduced osteoporosis from disuse of the fractured limb. The combination of a fixator of the invention and early patient mobilisation released hospital bed occupancy and nursing staff, with rapid healing of the fracture. This enabled the fixator to be removed within 3-6 months of fitting. The early results showed promise of rapid bone healing, and there was no observed evidence of excessive fracture movement or loss of bone length.

In the above tests, bone portion movement at the fracture site was measured to be up to 0.2 mm when load bearing. The corresponding relative movement between the fixed and guide clamps 227 and 228 when passively stimulated (see FIG. 7) within three weeks of the operation was between 0.2 mm and 0.5 mm. Part of the later movement was taken by bone screw flexing and part by strain at the fracture. Due to the construction of the fixator, lateral movement at the fracture is small, the main force component being loading axially of the fixated limb resulting in compressive strain. No distinction could be drawn between the passive stimulation regime in which actuated cyclical loading of the fracture commences for the patient one week after the operation, and active stimulation which followed when the patient got up, and walked with crutches at about two weeks post-operatively.

In one of the above operations involving both tibial and femoral fractures on different legs, the patient was not able to walk for about six weeks. However, the bone healing stimulus due to the passive or mechanically actuated regime was carried on for this period giving good radiological results. For part of the time the patient was also undergoing physiotherapy.

Parallel animal trials have been conducted to compare a prior art rigid fixator (UK Appln No. 7924853) with a fixator of the invention using passive stimulation. Osteotomised sheep tibiae were cyclically loaded using the invention with passive or mechanical actuation. The results compared with similarly prepared sheep with the prior art fixator. The sheep at other times walked about. X-ray and post-mortem mechanical data gave a clear indication that, at the two week and four week post-operative stages, the fixator of the invention produced more favourable results than the prior art device.

Table I gives details of four of the foregoing ten cases where patients completed a fracture management procedure, and the fixators (of the invention) on all four were removed following successful treatment.

TABLE I

| | | RELEVANT DATES AND REMARKS | | | |
|---|---|---|---|---|---|
| PATIENT | FRACTURE TYPE OR OPERATION | FIXATOR ON | BONE GRAFT OPERATION | FIXATOR OFF | COMMENTS |
| 1 | Severe, open fractured tibia, fibula, bone loss. Accident date 1.11.81. | 4.11.81 | 30.11.81 and one week passive stimulation | 15.3.82 | 21.4.82 full weight. No length loss. 3m. 15d. of fixation after operation. |
| 2 | Severe, open fractured tibia, fibula, bone loss. Traction applied. Date of accident 20.10.81. | 10.11.81 | 1.12.81 and one week passive stimulation | 22.3.82 | 21.4.82 healed solidly. 3m. 21d. of fixation after operation. |
| 3 | Polio. Leg lengthening. Left tibia. | 2.11.81 | 18.1.82 | 22.3.82 | Satisfactory. 2m. 4d. of fixation after operation. |
| 4 | Leg lengthening. Right tibia. | 10.8.81 | 16.11.81 | 8.2.82 | Satisfactory. 2m. 23d. of fixation after fixation. |

During the leg lengthening operation, each leg was progressively lengthened over a period of weeks, following which consolidation took place. To illustrate use of the fixator of the invention, FIG. 13 shows applied to a patient a fixator in accordance with FIG. 7. FIGS. 14 and 15 are similar and show the FIG. 2 device applied in an inverted manner.

We claim:

1. The method of using an external orthopaedic fracture fixator including a plurality of bone pins, and primary and secondary rigid supports therefor, which method comprises:

(a) transfixing opposed fragments of a bone relative to a fracture therein with respective different sets of said bone pins;
   (b) securing said sets of bone pins with respective ones of said supports;
   (c) interconnecting said supports to hold said fragments for reunion in a predetermined relationship aligned with an axis defined by said supports, while allowing relative bidirectional movements of said supports towards respective mutually expanded and contracted configurations thereof;
   (d) imposing a first limit on said movement along said supports towards said expanded configuration, which said first limit corresponds with said predetermined relationship;
   (e) continuously resiliently biasing said supports for relative movement towards said first limit;
   (f) imposing a second limit on said movement of said supports towards said contracted configuration, with the extent of movement between said first and second limits corresponding to a movement of said fragments which encourages callous formation without inhibiting primary bone formation; and
   (g) repetitively applying compressive force between said supports and between said fragments to move the former towards said second limit.

2. The method according to claim 1 wherein said movement extent is limited to up to about 0.5 mm at said fracture.

3. The method according to claim 1 wherein said movement extent is limited to up to 0.2 mm at said fracture when said bone is a tibia.

4. The method according to claim 1 wherein said movement extent is limited to up to 2.00 mm between said sets of pins at said supports.

5. The method according to claim 1 wherein said fixture further includes an actuator coupled between said supports to apply said compressive force, and which use comprises repetitively operating said actuator at about one cycle per second.

* * * * *